(12) United States Patent
Zhang (10) Patent No.: US 8,961,420 B2
(45) Date of Patent: Feb. 24, 2015

(54) SYSTEM FOR CARDIAC CONDITION DETECTION AND CHARACTERIZATION

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1135 days.

(21) Appl. No.: 12/947,882

(22) Filed: Nov. 17, 2010

(65) Prior Publication Data

US 2011/0245669 A1 Oct. 6, 2011

Related U.S. Application Data

(60) Provisional application No. 61/319,898, filed on Apr. 1, 2010.

(51) Int. Cl.
*A61B 8/00* (2006.01)
*A61B 8/08* (2006.01)
*A61B 8/12* (2006.01)

(52) U.S. Cl.
CPC .............. *A61B 8/0891* (2013.01); *A61B 8/12* (2013.01); *A61B 8/485* (2013.01)
USPC ........... 600/450; 600/437; 600/407; 600/441; 600/443

(58) Field of Classification Search
USPC ......... 600/407, 424, 427, 431, 437, 441, 443, 600/450
See application file for complete search history.

(56) References Cited

U.S. PATENT DOCUMENTS

| | | | |
|---|---|---|---|
| 5,771,895 A | 6/1998 | Slager | |
| 6,045,509 A | 4/2000 | Caro et al. | |
| 6,148,095 A | 11/2000 | Prause et al. | |
| 6,161,029 A | 12/2000 | Spreigl et al. | |
| 6,176,832 B1 | 1/2001 | Habu et al. | |
| 6,214,887 B1 | 4/2001 | Cote et al. | |
| 6,241,667 B1 | 6/2001 | Vetter et al. | |
| 6,254,543 B1 | 7/2001 | Grunwald et al. | |
| 6,371,921 B1 | 4/2002 | Caro et al. | |
| 6,547,734 B2 | 4/2003 | Madsen et al. | |
| 6,579,311 B1 | 6/2003 | Makower | |
| 6,656,207 B2 | 12/2003 | Epstein et al. | |
| 6,835,177 B2 | 12/2004 | Fritz et al. | |
| 6,882,886 B1 | 4/2005 | Witte et al. | |
| 7,022,077 B2 * | 4/2006 | Mourad et al. ................. | 600/449 |
| 7,074,188 B2 | 7/2006 | Nair et al. | |
| 7,139,614 B2 | 11/2006 | Scheiner et al. | |
| 7,189,231 B2 | 3/2007 | Clague et al. | |
| 7,209,777 B2 | 4/2007 | Saranathan et al. | |
| 7,215,802 B2 | 5/2007 | Klingensmith et al. | |

(Continued)

*Primary Examiner* — Joel Lamprecht
(74) *Attorney, Agent, or Firm* — Brennan K Bradley (57) ABSTRACT

A system monitors and characterizes internal elasticity of a blood vessel to detect abnormality. A catheter system for heart performance characterization and abnormality detection, comprises an ultrasound device for emitting ultrasound wave signals within patient anatomy and acquiring corresponding ultrasound echo signals. A signal processor processes the ultrasound echo signals to, determine a signal indicating displacement of a tissue wall over at least one heart cycle and identify a displacement value in the displacement signal. The displacement value indicates a tissue wall displacement occurring at a point within a heart cycle. A comparator compares the tissue wall displacement value with a threshold value to provide a comparison indicator. A patient monitor, in response to the comparison indicator indicating the tissue wall displacement value exceeds the threshold value, generates an alert message associated with the threshold.

21 Claims, 8 Drawing Sheets

(56) References Cited

U.S. PATENT DOCUMENTS

| | | |
|---|---|---|
| 7,285,097 B2 | 10/2007 | Tenerz et al. |
| 7,318,804 B2 | 1/2008 | Weitzel et al. |
| 7,338,452 B2 | 3/2008 | Shina et al. |
| 7,397,935 B2 | 7/2008 | Kimmel et al. |
| 7,409,240 B1 * | 8/2008 | Bishop .......................... 600/436 |
| 7,488,287 B2 | 2/2009 | Kawashima |
| 7,493,154 B2 | 2/2009 | Bonner et al. |
| 7,534,209 B2 | 5/2009 | Abend |
| 7,603,166 B2 | 10/2009 | Casscells et al. |
| 7,611,484 B2 | 11/2009 | Wellman et al. |
| 7,645,259 B2 | 1/2010 | Goldman |
| 7,647,831 B2 | 1/2010 | Corcoran et al. |
| 7,963,925 B1 * | 6/2011 | Schecter ....................... 600/508 |

* cited by examiner

SYSTEM FOR CARDIAC CONDITION DETECTION AND CHARACTERIZATION

This is a non-provisional application of provisional application Ser. No. 61/319,898 filed Apr. 1, 2010, by H. Zhang.

FIELD OF THE INVENTION

This invention concerns a catheter system for heart performance characterization and abnormality detection by processing ultrasound echo signals to identify a displacement value indicating a tissue wall displacement occurring at a point within a heart cycle and characterizing the wall displacement.

BACKGROUND OF THE INVENTION

Analysis of electrophysiological activity of surface ECG signals such as ECG (electrocardiogram) signals and intra-cardiac electrograms and time domain parameters of ECG waveforms is used for cardiac arrhythmia detection and diagnosis. The analysis is used to detect P wave disorders for atrial fibrillation (AF) and ST segment changes for myocardial ischemia and infarction, for example. However, known systems for cardiac arrhythmia identification and analysis based on ECG signals are subjective and need extensive expertise and clinical experience for accurate interpretation and appropriate cardiac rhythm management. Furthermore, there is a lack of an accepted standard or criteria for arrhythmia characterization and definition for ICEG signals (intra-cardiac electrograms). In addition to electrophysiological analysis, hemodynamic characteristics are utilized for cardiac pathology and event monitoring and detection, such as blood flow speed in a vessel, blood pressure deviation and hemodynamic excitation propagation in a blood vessel. IVUS (intra-vascular ultrasound) is also used to monitor and detect tissue characteristics and lesions inside a vessel.

Hemodynamic characteristics, such as blood pressure and blood vessel dynamics, are used for cardiac function and pathology detection, diagnosis and quantification. In response to a heart beat and chamber tissue squeezing, blood is pumped through arteries and generates systolic and diastolic blood pressure in artery and vein vessels. Heart derived blood pressure is measured by medical devices to extract heart tissue information and pathology status. For example, in AF (atrial fibrillation) or myocardial ischemia (MI), pumped blood volume and ventricle squeezing power may be reduced due to these pathologies, which may result in drop of blood pressure in an artery and vein vessel. The deviation and changes of blood pressure also affect dynamic characteristics of vessel tissue, especially a tissue wall.

Known monitoring systems fail to adequately detect and characterize arrhythmia and cardiac function using internal blood vessel dynamic mode changes. Known ECG signal and hemodynamic pressure signal monitoring systems fail to accurately and comprehensively track location and timing of a disease and malfunction, such as AF. A system according to invention principles addresses these deficiencies and related problems.

SUMMARY OF THE INVENTION

A system monitors and characterizes internal elasticity of a blood vessel and focal vibration of a vessel wall, to capture, diagnose and characterize small changes in a blood vessel during blood propagation in the vessel. A catheter system for heart performance characterization and abnormality detection, comprises an ultrasound device for emitting ultrasound wave signals within patient anatomy and acquiring corresponding ultrasound echo signals. A signal processor processes the ultrasound echo signals to, determine a signal indicating displacement of a tissue wall over at least one heart cycle and identify a displacement value in the displacement signal. The displacement value indicates a tissue wall displacement occurring at a point within a heart cycle. A comparator compares the tissue wall displacement value with a threshold value to provide a comparison indicator. A patient monitor, in response to the comparison indicator indicating the tissue wall displacement value exceeds the threshold value, generates an alert message associated with the threshold.

DETAILED DESCRIPTION OF THE INVENTION

A system monitors internal elasticity of a blood vessel and focal vibration patterns of a vessel wall, to capture, diagnose and characterize small changes in a blood vessel during blood propagation in the vessel. The system calculates statistical variation of blood vessel elasticity and other patient signals (vital sign signals, EP signals, such as blood pressure, ECG, ICEG signals, SPO2 (blood oxygen saturation)) as well as the location, severity and heart cycle timing of cardiac pathology including myocardial ischemia and atrial fibrillation. The system characterizes cardiac vessel flexibility and elasticity for identifying cardiac disorders, differentiating cardiac arrhythmias, characterizing pathological severity, predicting life-threatening events, and evaluating effect of drug delivery.

The system determines vessel flexibility and elasticity characteristics (including of an artery and vein) to monitor patient health status and determines cardiac arrhythmia and pathologies from vessel wall movement and dynamics. There are many causes of cardiac malfunctions and disease, such as aging, diet and lack of exercise. These causes of cardiac conditions first affect a blood vessel from inside, such as via a blockage, calcium or stiffness. Small physical events or arrhythmias and cardiac function deviation (e.g., in early stage pathologies) may not show up in electrophysiological signals (including surface ECG signals and ICEG signals).

The system performs deviation calculation and mode tracking of vessel wall dynamics and movements and derives parameters to characterize hemodynamic signal variation and variability. The system analysis of blood vessel characteristics is different from blood pressure analysis (such as of invasive chamber blood pressures).

The system advantageously determines dynamic blood vessel response which may be significant for pathology detection. Some arrhythmias, such as MI, may affect blood vessel characteristics more than pressure. Also deviation in synchronization between pressure signals and wall dynamic response are advantageously used for localization and timing identification of heart function and diseases. The system determines blood vessel dynamics involving associating structural mode and pattern changes that occur in collagen and elastic fibers with changes in viscoelastic behavior that are associated with cardiac function and arrhythmias. The system in one embodiment uses information acquired using an IVUS catheter, to facilitate determination of physical reasons and sources of cardiac pathologies from inside of the blood circulation system.

In one embodiment the system uses information acquired by an IVUS system to analyze flexibility and elasticity of a blood vessel (both artery and vein), to detect and quantify vessel stiffness early on. In another embodiment internal cardiac blood vessel dynamic monitoring and mode analysis is used to track and diagnose movement and abnormality in vessel hemodynamic characteristics to identify a vessel problem and cardiac malfunction, such as myocardial ischemia. The system also performs a combined signal analysis involving analysis of vessel dynamic signals (waveform, data and pattern) together with synchronized patient signals, such as surface ECG and ICEG signals. This combined analysis of different data and signals is used to detect cardiac tissue and function abnormality or events. The system uses information acquired with different kinds of sensors and transducers such as mechanical vessel or blood flow sensors located in invasive catheter internal leads. The acquired information indicates vessel or tissue movement and dynamic characteristics. The internal signal cardiac analysis is not limited to IVUS information. The analysis and calculation may be used in an ICD (implantable cardiac devices) for cardiac function and tissue monitoring and evaluation.

The system vessel dynamic analysis is combined with other internal or external imaging data (such as from X-Ray, MRI). In operation, imaging is used to find a suspect vessel or tissue area for IVUS and a local IVUS catheter is used to acquire imaging and related information for vessel wall dynamic analysis, calculation and characterization. The system compares acquired information to detect abnormality and events for different stages in a hemodynamic blood cycle. The system also compares information derived for different vessels and areas within a vessel to identify deviation and variation. System vessel vibration analysis is not limited to an IVUS application. An external ultrasound or microwave based blood vessel wall tracking system may also be used in non-invasive data acquisition.

An IVUS provides blood vessel imaging and scanning, to facilitate detection of vessel physical defects, such as calcium and thrombosis. In one embodiment the system uses real time wall dynamic and vibration detection employing an IVUS system and analyzes patterns of blood wall elasticity dynamic characteristics during heart excitation and cardiac arrhythmia, for example. The system performs multi-channel signal acquisition using different types of catheter for IVUS vessel wall dynamic monitoring and calculates vessel wall parameters and elasticity for cardiac arrhythmia detection based on vessel wall dynamic rhythm determination (time and position based determination including bi-lateral comparison of parallel walls), for example. Known IVUS catheters use ultrasound to detect and localize wall position with a certain direction and angle. It is difficult to use a known IVUS catheter to achieve real time blood vessel wall movement pattern tracking and interpretation.

Figure 1:
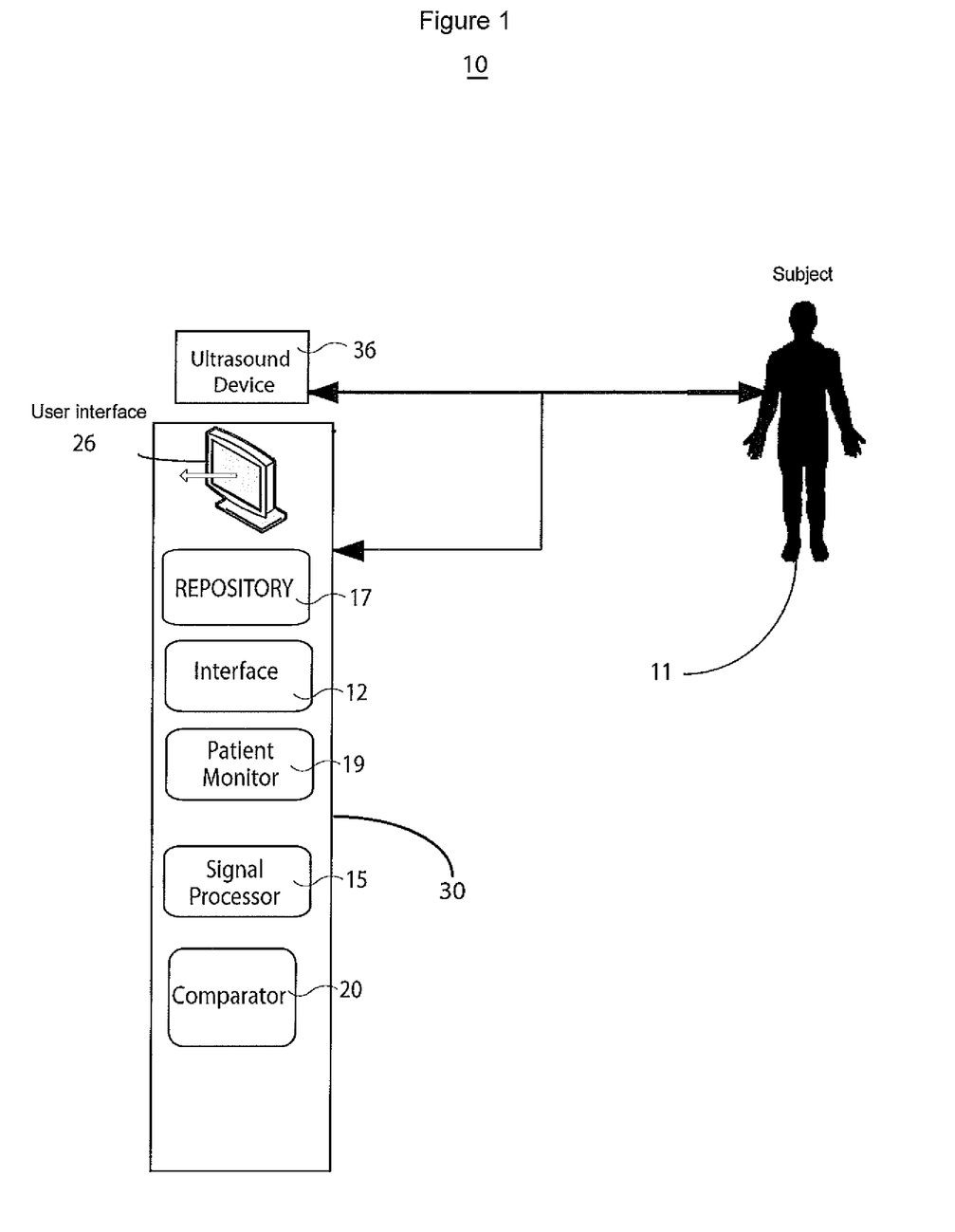
FIG. 1 shows a system for heart performance characterization and abnormality detection, according to invention principles.

FIG. 1 shows system 10 for heart performance characterization and abnormality detection. System 10 comprises ultrasound device 36 and at least one computer system, workstation, server or other processing device 30 including interface 12, repository 17, patient monitor 19, signal processor 15, comparator 20 and a user interface 26. Ultrasound device 36 emits ultrasound wave signals within patient 11 anatomy and acquires corresponding ultrasound echo signals. Signal processor 15 processes the ultrasound echo signals to determine a signal indicating displacement of a tissue wall over at least one heart cycle and identify a displacement value in the displacement signal. Alternatively interface 12 acquires tissue displacement representative signals indicating displacement of a tissue wall over at least one heart cycle. The displacement value indicates a tissue wall displacement occurring at a point within a heart cycle. Comparator 20 compares the tissue wall displacement value with a threshold value to provide a comparison indicator. Patient monitor 19 in response to the comparison indicator indicating the tissue wall displacement value exceeds the threshold value, generates an alert message associated with the threshold. Repository 17 incorporates predetermined mapping information, associating ranges of the displacement value or values derived from the displacement value, with corresponding medical conditions. Comparator 12 compares the displacement value or values derived from the displacement value, with the ranges to provide a comparison indicator identifying a medical condition and patient monitor 19 generates an alert message identifying the medical condition.

Figure 2:
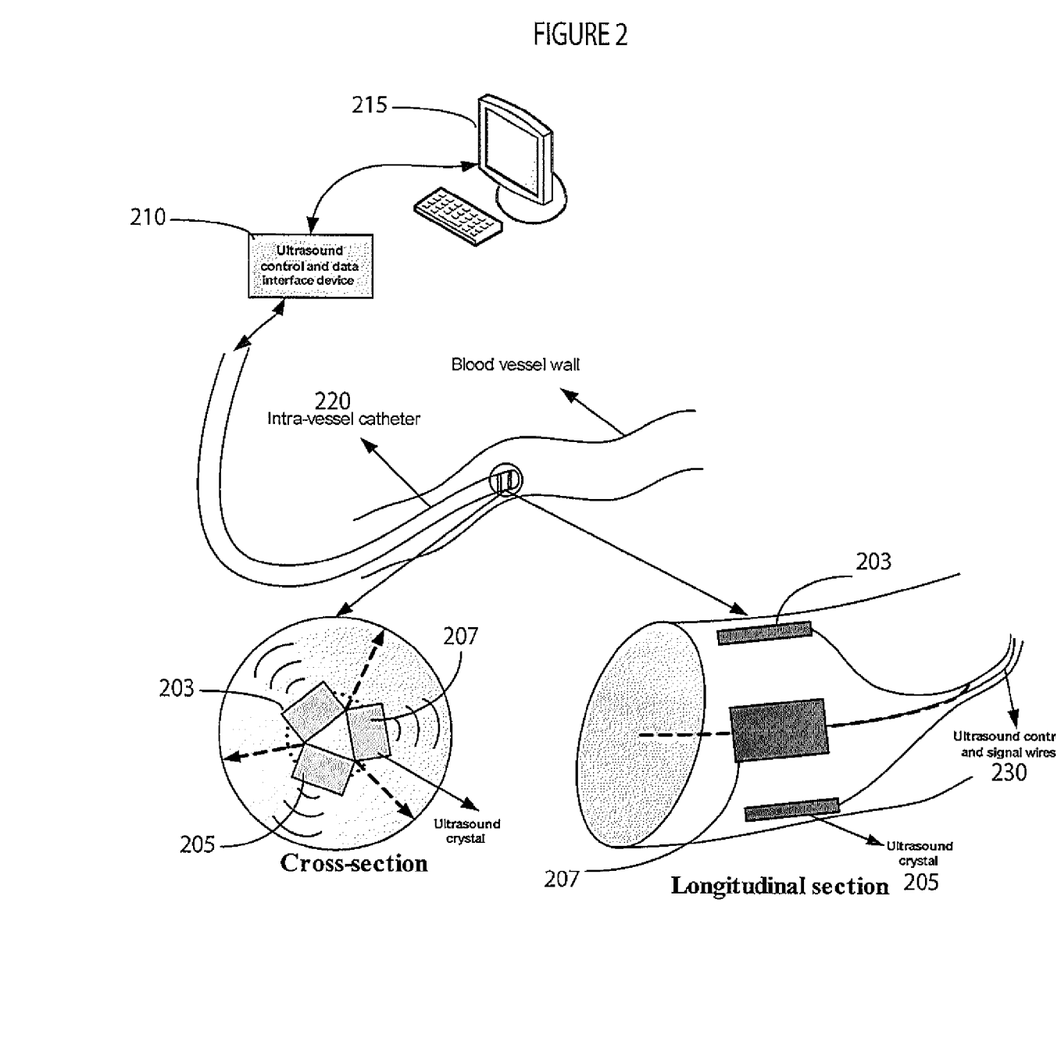
FIG. 2 illustrates intra-vessel ultrasound catheter blood vessel wall monitoring, according to invention principles.

Ultrasound wave scattering echoes resulting from corresponding wave emission may extend to 120 degrees depending on blood vessel tissue material properties and blood medium. FIG. 2 illustrates intra-vessel ultrasound catheter blood vessel wall monitoring using three emission and reception crystals 203, 205 and 207. The system is not limited to ultrasound application, and can be used for other types of wave radiation, such as different frequency microwave emission, for example. An intra-vessel catheter 220 for blood vessel wall movement tracking and analysis employs ultrasound crystals 203, 205 and 207 and covers 360 degrees to achieve real time vessel cross-section mapping and imaging. The ultrasonic wave control and wave reception data is bi-directionally transmitted through wires 230 between catheter 220 and control and signal interface unit 210. Ultrasound control and signal interface unit 210 filters and digitizes signals and provides the filtered digitized data to unit 215. Computer processing and visualization unit 215 processes the received filtered digitized data to provide real time vessel cross section images and calculates elasticity and flexibility due to heart beat excitation.

Ultrasound control and signal interface unit 210 applies voltage to ultrasound crystals and the crystals create ultrasound waves which are used to measure and detect vessel wall movement and positions. The received ultrasound echo waves are converted by crystals 203, 205 and 207 to electrical signals transmitted by electrical wires 230 to ultrasound control and signal interface unit 210. The ultrasound waves are deconvoluted, filtered and reconstructed by unit 210 to provide data used by unit 215 for visualization of a blood vessel and to derive wall dynamic movement and elasticity information during heart beat excitation. Computer processing and visualization unit 215 processes data acquired using intra-vessel catheter 220 to provide vessel position, angulation and vessel movement data. The noise from the catheter movement, patient respiration, and electrical noise, is filtered and extracted by using synchronizing signals including respiratory signals. Movement of an intra-vessel catheter is made manually or automatically by device. The speed of movement of a catheter during insertion and the angle of catheter rotation are accurately recorded in association with corresponding ultrasound echo data.

Figure 3:
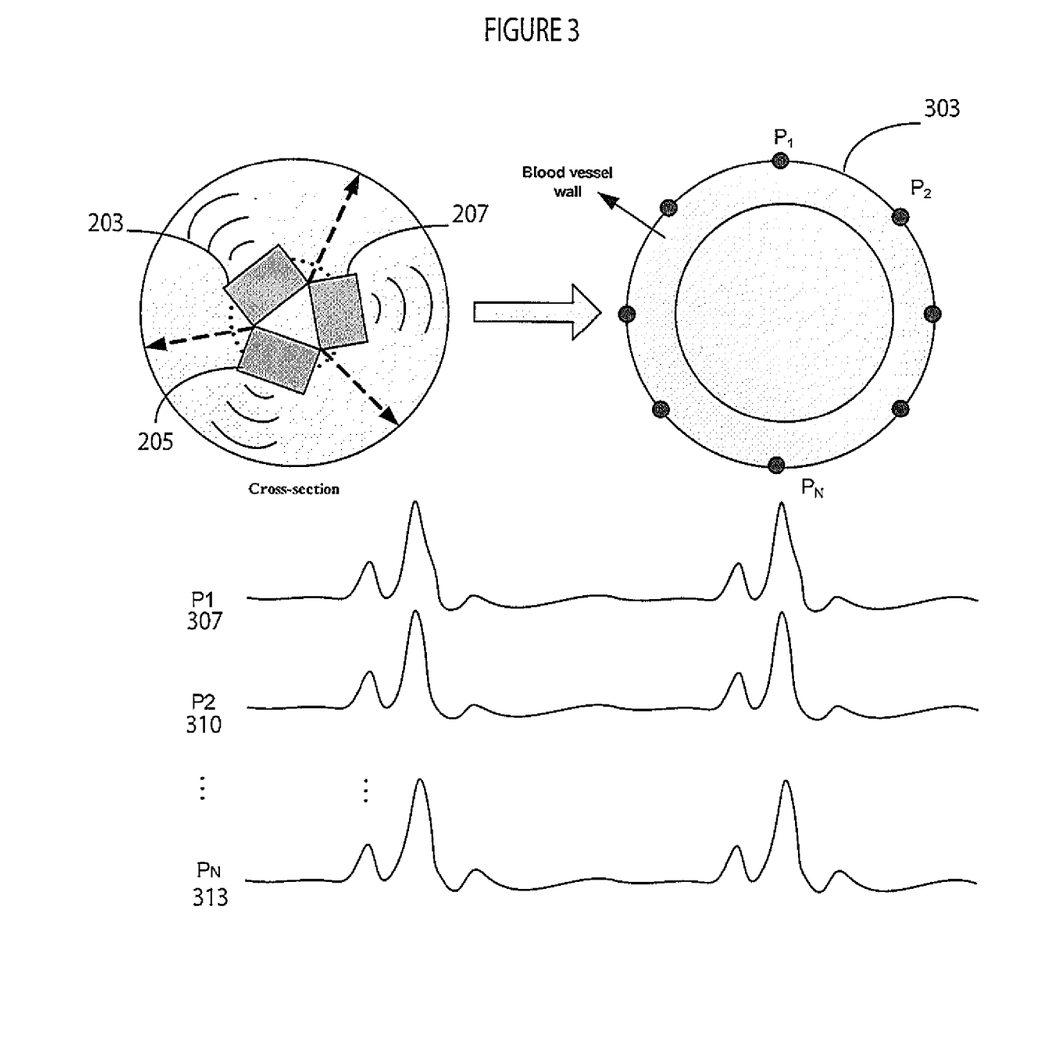
FIG. 3 shows multi-point based vessel wall dynamic vibration waveforms, according to invention principles.

FIG. 3 shows multi-point based vessel wall dynamic vibration waveforms. In a vessel cross section plane there may be multiple points (P1, P2 . . . $P_N$) for a user to select to be used for wall dynamic and vibration rhythm monitoring and calculation. Vessel cross section 303 shows an example with eight selected wall points for blood vessel vibration monitoring. Each position of the eight points is used to determine wall elasticity during each heart beat cycle. A wall displacement (vibration) waveform for each selected vessel wall point is derived (307, 310 . . . 313) by using ultrasound based vessel wall movement analysis and derived waveforms are used to analyze heart rhythm. For example, each selected vessel wall point (e.g. $P_N$) is dynamically vibrating due to heart rate and internal vessel blood pressure variation. System 10 (FIG. 1) calculates vessel wall movement displacement from ultrasound echo data in real time and provides a one dimensional displacement signal for each selected wall point. System 10 uses multi-position based vessel vibration mode analysis of an LAD (Left Anterior Descending) vessel or RCA (Right Coronary Artery) vessel, for example, using different positions in a longitudinal section to identify blockage and disease within a vessel, such as calcium blockage in the vessel. In one embodiment, ICEG (intra-cardiac electrogram) catheters are inserted, and ultrasonic waveform based wall dynamic vibration mode analysis is performed. In order to get good resolution in waveform analysis, the sampling rate of the waveform may be between 50 and 2000 Hz. The higher the frequency sampling of the waveform, the more detailed information is extracted and characterized by system 10 variability analysis.

System 10 analyzes and compares data at different vessel cross sectional and longitudinal positions and determines vessel vibration rhythms and cardiac pathology and abnormality and identifies blood (hemodynamic) wall movement patterns indicating rhythms. If blood pressure (such as systolic and diastolic pressures) remains constant, but the vessel has some physical changes, such as plague, calcium or stiffness, the amplitude and variation of vessel dynamic vibration due to a heart beat or hemodynamic pressure flow is reduced. If a vessel is normal without any stiffness or additional blockage, the vessel wall (muscle tissue) response reflects the cardiac functions and events, such as myocardial ischemia, atrium fibrillation.

Figure 4:
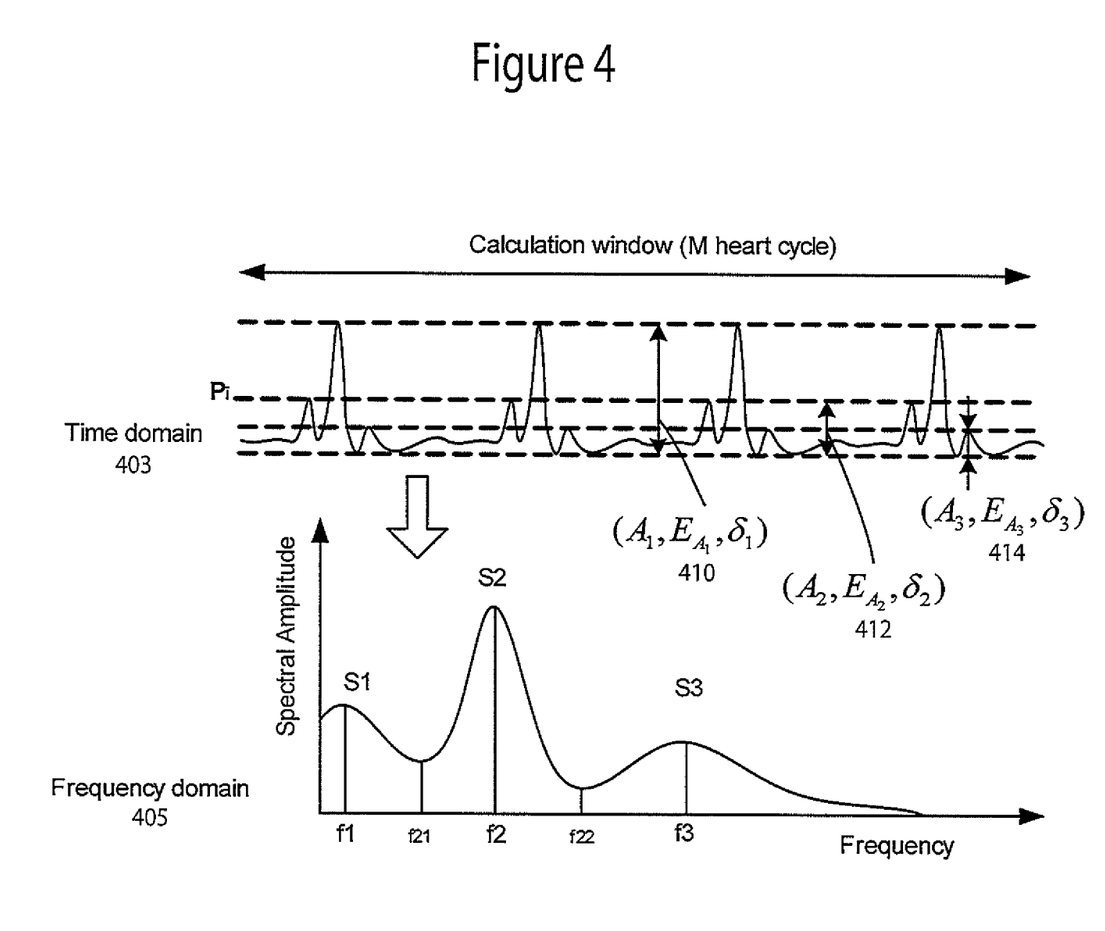
FIG. 4 shows time and frequency domain signal distribution for blood vessel dynamic vibration analysis, according to invention principles.

FIG. 4 shows time domain 403 and frequency domain 405 signal distribution for blood vessel dynamic vibration analysis performed using a window shifting calculation. The calculation of the blood vessel wall dynamic vibration is performed over a multi-beat heart cycle window. The number of cycles is adaptively determined based on noise level (indicated by signal to noise ratio) and desired calculation precision. The time and frequency domain signal characteristics 403 and 405 are determined over four heart cycle signals, for example. Time domain signal data 403 is used by system 10 (FIG. 1) to calculate amplitude (magnitude) changes, average value, standard deviation and windowed multi-cycle based signal variation and variability and pattern changes. Frequency domain signal 405 is used by system 10 to determine different peaks representing spectrum energy which reflects vessel wall vibration energy and energy changes and a highest peak in the spectrum and peak ratios are used for determining cardiac excitation variation. Correspondingly, a vibration pattern is used to determine the deviation of cardiac depolarization or repolarization.

A multi-cardiac cycle window is used by system 10 for time domain variation analysis. For instance, four heart beats are used in an example. There are typically three peaks in a time domain vessel vibration signal waveform, A1 peak 410 which corresponds to an R wave and QRS complex in ECG signals (that may be used for ischemia and infarction detection, ventricular tachycardia detection), A2 412 represents the waveform of an atrium which is a P wave in the ECG waveform (that may be used for atrial fibrillation detection), A3 414 represents a repolarization waveform, which is a T wave in the ECG signals (that may be used for ventricular fibrillation, myocardial infarction). System 10 analyzes different waveform changes representing blood vessel wall dynamic vibration to detect and quantify changes in different vessel portions indicating cardiac function and electrophysiological changes. Amplitude A1 wave is typically used in blood vessel wall vibration characterization. For each wave Ai, different parameter values are calculated using a shifting window including, an averaging amplitude $E_{A_i}$, and a standard deviation for the wave $\delta_i$. (The following equations are used by system 10 for different waves in the signals)

$$\text{Amplitude changes: } \Delta\% \ (A_i(t)) = \left| \frac{E_{A_i(t)} - E_{A_i(base)}}{E_{A_i(base)}} \right|$$

$$\text{Standard deviation changes: } \Delta\% \ (\delta(t)) = \left| \frac{\delta_{A_i(t)} - \delta_{A_i(base)}}{\delta_{A_i(base)}} \right|$$

$$\text{Wave variation: } \text{Var}(A_i(t)) = \left| \frac{E_{A_i(t)}}{\delta_{A_i(t)}} \right|$$

In which, $A_i$(base) is the waveform Ai in a reference signal selected by a user or system 10 as a threshold for comparison and for warning generation.

System 10 converts blood vessel dynamic vibration signal data to other domains including a frequency domain as illustrated in the frequency spectrum 405 showing multiple peaks. Each peak represents energy or frequency components. System 10 monitors the peak spectral values and shift in frequency of the peaks as well as deviations in patterns. For example, there are three peaks in the frequency domain distribution (but there may be more peaks). According to the sequence in the domain, they are, S1, S2, S3 and corresponding frequencies are f1, f2, f3. The highest peak is defined as a principal component frequency which reflects the main energy dynamic component. The deviation of the principal component is used to track and detect the vessel vibration pattern variation. System 10 determines energy and frequency ratio as, $$\text{Instantaneous ratio:} = \frac{|S_i|^2}{f_i},$$

in which i represents the wave peak i.

$$\text{Average ratio} = \sum_{j \in i} \frac{|S_{ij}|^2}{f_{ij}},$$

in which j are the discrete values for frequency bandwidth of Si; for example in FIG. 4, the area of the S2 is from f21 to f22 (between nearest valleys of the waveform of Si).

$$\text{Spectral ratio} = \left| \frac{S_{N1} - S_{N2}}{S_{N1} - S_{N3}} \right|,$$

In which $S_{N1}$ represents the highest spectral peak value (principal component) and $S_{N2}$, $S_{N3}$ represent the second and third peak component respectively.

System 10 also performs time-frequency combined domain analysis involving wavelet based singularity detection in a 1D (one dimensional) signal waveform, symbolic complexity analysis, entropy analysis and pattern tracking. System 10 uses time synchronization between a blood vessel wall vibration 1D waveform and other patient signals (such as ECG signal, SPO2 signal, ICEG signal) to detect and identify cardiac arrhythmias. For example, synchronizing latency (duration) variation between R wave and a maximum amplitude wave in the time domain (A1 peak) is used as a parameter to describe and quantify cardiac function variation and pathologies. Different time sequences or episodes of the same vessel are used for cardiac arrhythmia or event detection since different episodes may reflect cardiac cycle excitation variation.

Figure 5:
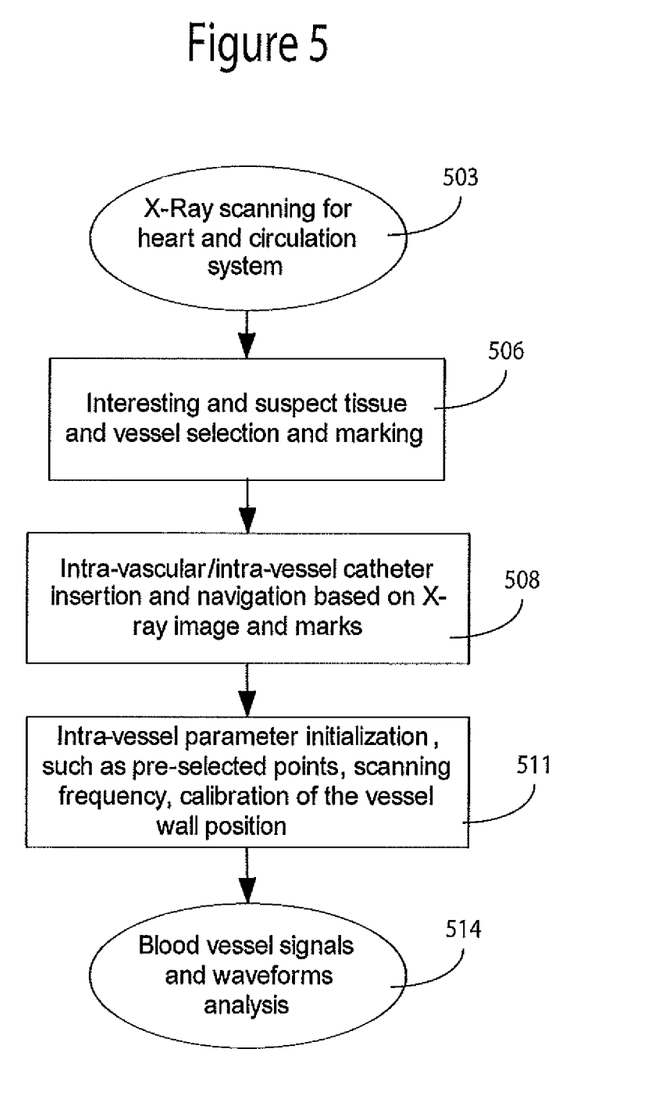
FIG. 5 shows a flowchart of a process for (X-Ray or MRI) image acquisition of heart and circulation and identifying interesting (good or diseased) vessels, according to invention principles.
Figure 6:
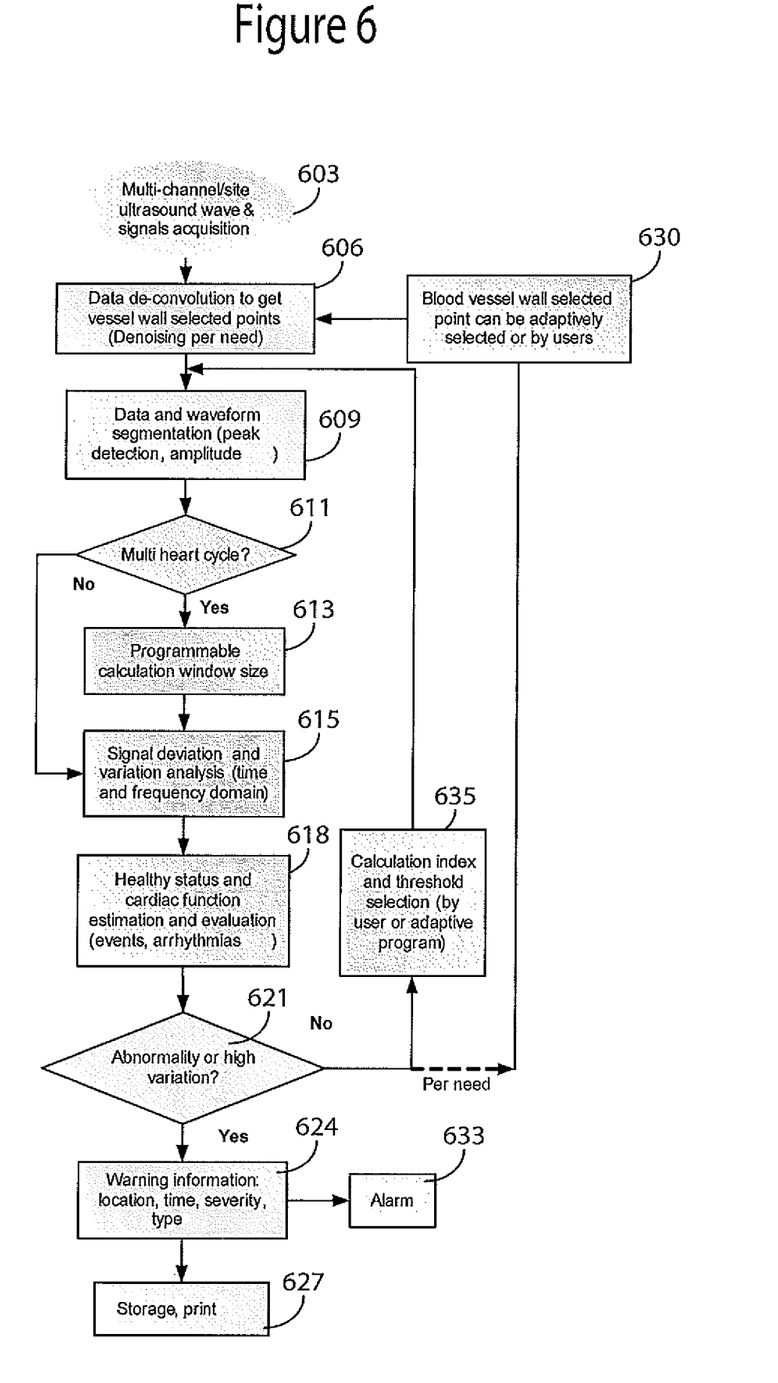
FIG. 6 shows a flowchart of a process for blood vessel dynamic vibration mode and pattern analysis and detection of cardiac pathology, according to invention principles.

FIGS. 5 and 6 show methods for navigation and selection of vessels and positions for intra-vessel (intra-vascular) ultrasound examination and illustrate blood vessel dynamic vibration signal analysis for detection of cardiac pathologies and events based on blood vessel wall movement variation and variability. FIG. 5 shows a flowchart of a process for (X-Ray or MRI) image acquisition of heart and circulation and identifying interesting (good or diseased) vessels. In step 503 an X-ray system acquires images of a heart and circulation system and interesting and potentially abnormal tissue is automatically (or manually by a user) identified and marked in step 506. A user inserts and guides an ultrasound catheter to a desired location in response to the marked tissue location in step 508. In step 511 system parameters are initialized by system 10 selection of vessel points and scanning frequency and calibration of wall position data. System 10 in step 514 performs vessel wall analysis as previously described using the initialized parameters and the ultrasound catheter.

FIG. 6 shows a flowchart of a process for blood vessel dynamic vibration mode and pattern analysis and detection of cardiac pathology. In step 603 ultrasound catheters of device 36 (FIG. 1) acquire ultrasound data on multiple channels from multiple vessel sites and the acquired data is de-convoluted in step 606 to provide ultrasound waveform data of selected points of a vessel wall. In step 609, signal processor 15 identifies different segments (QRS, ST, P wave, Q wave, R wave, S wave, ST segment, T wave, U wave segments, for example) of the ultrasound waveform data. In step 611, if system configuration data indicates a single heart cycle analysis is to be performed, processor 15 performs time domain and frequency domain vessel wall analysis including vessel wall displacement calculation, displacement deviation and variation analysis, in a single heart cycle in step 615. In step 611, if system configuration data indicates a multiple heart cycle analysis is to be performed, processor 15 determines a heart cycle window size in step 613 and performs time domain and frequency domain vessel wall analysis including vessel wall displacement calculation, displacement deviation and variation analysis, in the determined multiple heart cycle window in step 615.

In step 618, signal processor 618 uses repository 17 of predetermined mapping information, associating ranges of vessel wall displacement values or values derived from the displacement value, with corresponding medical conditions. Comparator 20 compares the displacement value or values derived from the displacement value with thresholds and with the ranges in step 621 to provide a comparison indicator identifying a medical condition or abnormality. If no abnormality is determined system 10 selects a different vessel point in step 630 and iteratively repeats steps 606-621 or alternatively (depending on application or user selection) system 10 in step 635 adjusts a threshold, or type of calculation performed and iteratively repeats steps 606-621. If an abnormality is detected in step 624, patient monitor 19 generates an alert message identifying the. location, severity and time of occurrence within a heart cycle of a medical condition and records or prints this information in step 627 and generates an associated alarm message in step 633.

The blood vessel wall dynamic vibration analysis is not limited to a cardiac cycle and pathology monitoring and is used to track hemodynamic characteristic changes for early detection of heart function deviations. Different kinds of artifacts may affect blood vessel dynamic vibration waveform signals, such as respiration artifacts, power line noise, and other biological noises of a patient. The system reduces noise and artifacts by synchronized intra-vessel ultrasound signal scanning and wall dynamic detection. For example, a user selects a respiration peak time and delays signal calculation for 0.2-1 seconds to reduce effects of body movement. Different filters, such as high pass filter (0.5-5 Hz) or band pass filters are adaptively selected to eliminate the noise and unwanted artifacts in the signals. The vessel dynamic analysis is performed at a specific vessel position as well as for a moving catheter. In this way, a single vessel position (unilateral) vessel dynamic mode and pattern cardiac arrhythmia are analyzed. The system performs calculations for multiple (at least two) vessel positions for vessel dynamic pattern analysis to identify cardiac arrhythmias as well as vessel elasticity.

Figure 7:
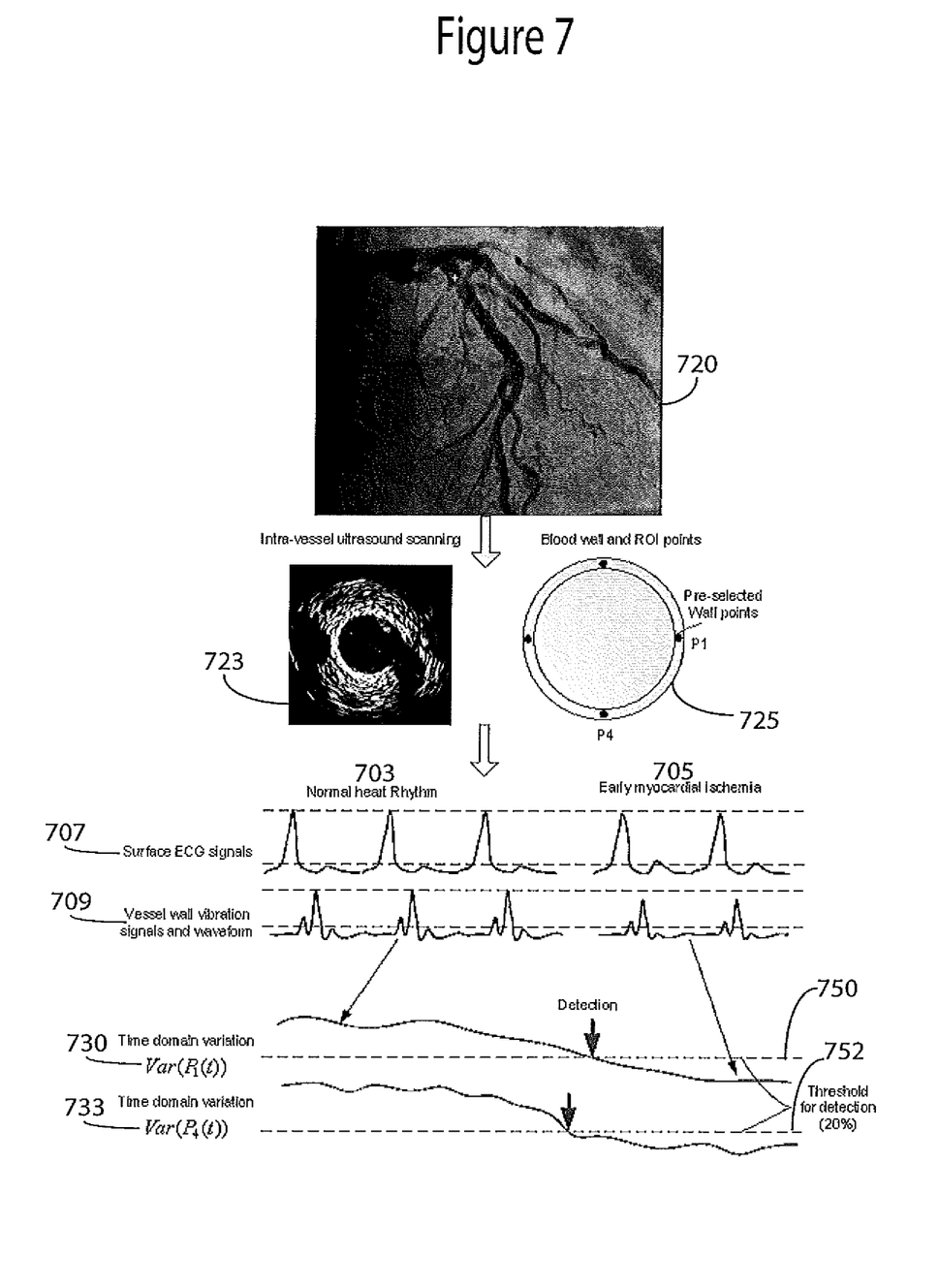
FIG. 7 illustrates blood vessel dynamic vibration analysis based cardiac arrhythmia detection, according to invention principles.

FIG. 7 illustrates blood vessel dynamic vibration analysis based cardiac arrhythmia detection using single vessel analysis at four different pre-selected points on a vessel wall. A user acquires an X-ray image 720 to find an interesting region of interest (ROI) in a circulation system, inserts an Intra-vascular ultrasound catheter into the ROI area and acquires ultrasound image data 723 and determines a position, wall boundary and wall points (P1, P2, P3, P4) for dynamic vibration waveform acquisition 725. System 10 acquires signals for the selected blood vessel wall points. FIG. 7 illustrates comparison of two episodes, normal heart rhythm 703 versus early myocardial ischemia (MI) 705 episodes. Surface ECG signal waveforms 707 exhibit small amplitude and period T changes between normal 703 and early myocardial ischemia (MI) 705 waveforms. However, change in ST segment is only 0.02 mV, substantially less than the 0.1 mV standard MI detection threshold. System 10 analyzes the vessel dynamic vibration amplitude 709 (here, time domain amplitude of an A1 peak is used for analysis but different methods may be used for calculation) and determines variation waveforms Var 730 and 733 of P1 and P4 respectively. Peak to peak Var during the normal heart rhythm is 4.5 and peak to peak Var of early MI is 3.1, which shows the Var calculation variation is about 30%. The variation of the two episodes exceeds 20% thresholds 750 and 752 of Var waveforms 730 and 733 respectively. Thresholds 750 and 752 are adaptively adjusted by system 10 to detect abnormality in response to previous detection data and thresholds. Hence system 10 accurately and reliably detects an MI event. Additionally, by analyzing wall displacement at multiple positions of a blood vessel, the location, severity and timing of cardiac pathology and arrhythmia are determined for coronary artery analysis, for example.

Figure 8:
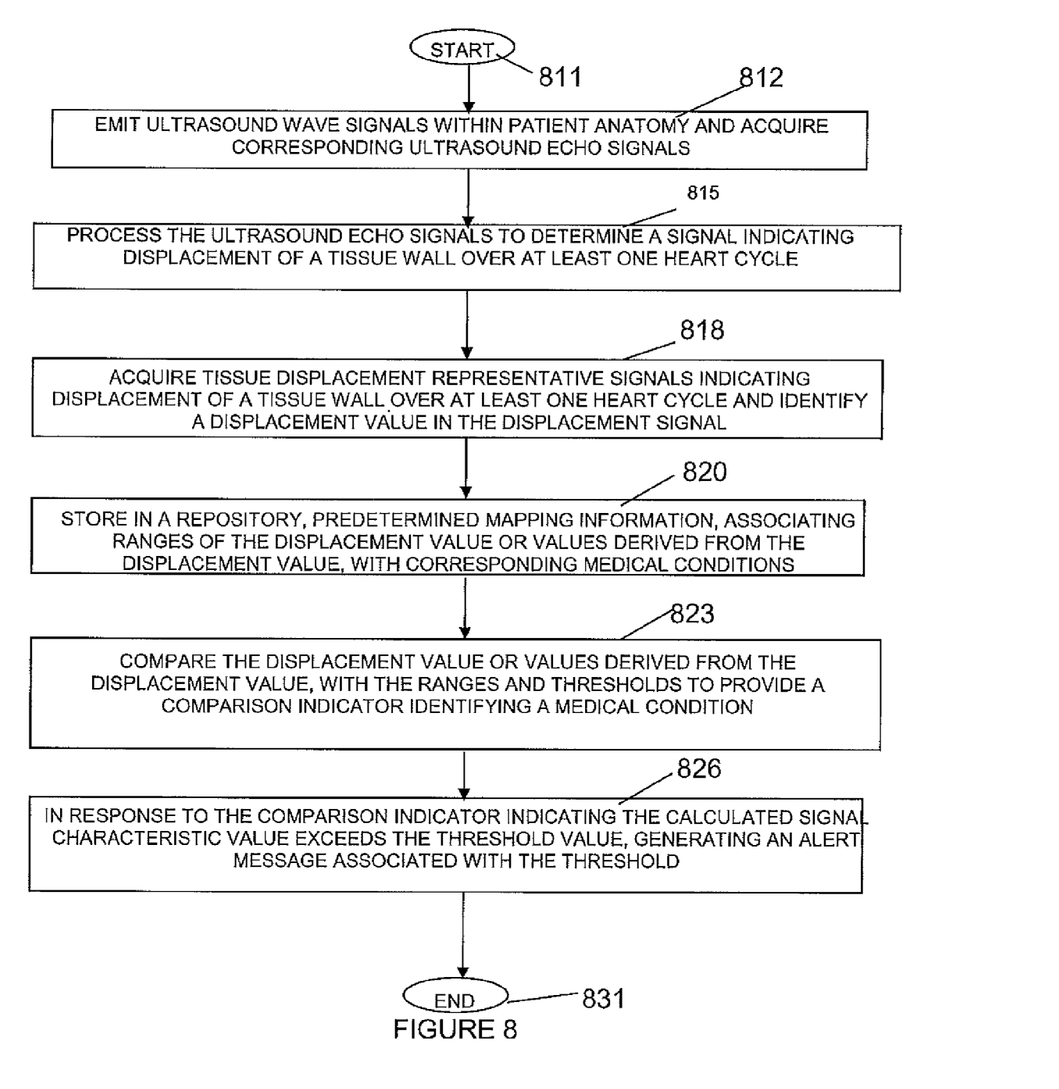
FIG. 8 shows a flowchart of a process used by a system for heart performance characterization and abnormality detection, according to invention principles.

FIG. 8 shows a flowchart of a process used by patient treatment monitoring system 10 (FIG. 1). In step 812 following the start at step 811, ultrasound device 36 emits ultrasound wave signals within patient anatomy and acquires corresponding ultrasound echo signals at a sampling rate of 50-2000 Hz. Ultrasound device 36 includes multiple transducers arranged substantially symmetrically within a catheter for emitting ultrasound wave signals substantially perpendicular to a catheter longitudinal axis, for determining vessel wall dynamic movement over a heart cycle or respiratory cycle. In step 815, signal processor 15 processes the ultrasound echo signals to determine a signal indicating displacement of a tissue (vessel) wall over at least one heart cycle comprising a digitized electrical signal. In step 818 processor 15 identifies a displacement value (a peak to peak displacement value) in the displacement signal (or tissue displacement representative signals acquired by interface 21 that indicates displacement of a tissue wall over at least one heart cycle) where the displacement value indicates a tissue wall displacement occurring at a predetermined point of a heart beat cycle in response to a synchronization signal.

In one embodiment, signal processor 15 calculates the displacement value by averaging multiple corresponding respective displacement values determined at substantially the same point in a heart cycle and over multiple heart cycles. Processor 15 determines a displacement value in the displacement signal comprising at least one of, (a) a second highest peak to peak displacement value and (b) a third highest peak to peak displacement value indicating a tissue wall displacement occurring at a point within a heart cycle. Signal processor 15 also determines the displacement value in the displacement signal and derives at least one value from the displacement value. The at least one derived value includes at least one of, (a) an averaged displacement value determined by averaging multiple corresponding respective displacement values determined at substantially the same point in heart cycle and over multiple heart cycles and (b) a standard deviation of the displacement value for a particular heart cycle. Processor 15 further derives at least one value from the displacement value including at least one of, $$\text{Amplitude change: } \Delta\% \ (A_i(t)) = \left| \frac{E_{A_i(t)} - E_{A_i(base)}}{E_{A_i(base)}} \right| \quad \text{(a)}$$

-continued $$\text{Standard deviation change: } \Delta\% \ (\delta(t)) = \left| \frac{\delta_{A_i(t)} - \delta_{A_i(base)}}{\delta_{A_i(base)}} \right| \quad \text{(b)}$$

and $$\text{Wave variation: } \text{Var}(A_i(t)) = \left| \frac{E_{A_i(t)}}{\delta_{A_i(t)}} \right| \quad \text{(c)}$$

where, for each wave Ai, $E_{A_i}$ is an averaged amplitude, $\delta_i$ is a standard deviation for the wave and $A_i$(base) is the waveform Ai in a preselected reference signal.

In a further embodiment, signal processor 15 derives at least one value from the displacement value comprising a value representing a spectrum characteristic of a bandwidth encompassing a displacement peak amplitude value. Processor 15 derives at least one value from the displacement value including at least one of, $$\text{a ratio:} = \frac{|S_i|^2}{f_i}, \quad \text{(a)}$$

in which i represents a wave peak i and $$\text{ratio} = \left| \frac{S_{N1} - S_{N2}}{S_{N1} - S_{N3}} \right|, \quad \text{(b)}$$

where $S_{N1}$ represents a highest spectral peak value and $S_{N2}$, $S_{N3}$ comprise the second and third peak components respectively.

Processor 15 in step 820 stores in repository 17, predetermined mapping information, associating thresholds and ranges of the displacement value or values derived from the displacement value, with corresponding medical conditions. The predetermined mapping information associates ranges of the displacement value or values derived from the displacement value, with particular patient demographic characteristics and with corresponding medical conditions and the system uses patient demographic data including at least one of, age, weight, gender and height in comparing the displacement value or values derived from the displacement value with the ranges. Signal processor 15 dynamically adjusts the threshold value in response to a determined sensitivity of arrhythmia detection. A threshold value is derived from recorded displacement signal data of the tissue wall for the patient or is derived from recorded displacement signal data of a tissue wall for a population of patients. The population of patients has similar demographic characteristics that include at least one of, (a) age, (b) weight, (c) gender and (d) height, to those of the patient. In step 823, comparator 20 compares the displacement value or values derived from the displacement value, with the thresholds and ranges to provide a comparison indicator identifying a medical condition. Patient monitor 19 in step 826 generates an alert message identifying the medical condition in response to the comparison indicator indicating the tissue wall displacement value exceeds the threshold value or lies in a predetermined value range and substantially continuously monitors the comparison indicator for at least a 24 hour period. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 analyzes and compares wall displacement data and time and frequency domain parameters derived from wall displacement data with predetermined thresholds and ranges to identify medical conditions. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both.

What is claimed is:

1. A catheter system for heart performance characterization and abnormality detection, comprising:
   an ultrasound device configured to emit ultrasound wave signals within a vessel of patient anatomy and acquire corresponding ultrasound echo signals, said ultrasound device comprising a plurality of sensors, each sensor configured to emit the ultrasound wave signals within the vessel and acquire the corresponding ultrasound echo signals covering at least 120 degrees of an internal circumference of a tissue wall of the vessel;
   a signal processor configured to process the ultrasound echo signals to:
      determine a displacement signal indicating displacement of a tissue wall over at least one heart cycle; and
      identify a displacement value in the displacement signal, said displacement value indicating a tissue wall displacement of the tissue wall of the vessel occurring at a point within a heart cycle;
   a comparator configured to compare the tissue wall displacement value with a threshold value to provide a comparison indicator; and
   a patient monitor configured to generate an alert message associated with the threshold in response to said comparison indicator indicating the tissue wall displacement value exceeds the threshold value.

2. A system according to claim 1, wherein
said patient monitor, in response to said comparison indicator indicating the tissue wall displacement value lies in a predetermined value range, generates an alert message associated with the value range.

3. A system according to claim 2, wherein
said patient monitor substantially continuously monitors said comparison indicator for at least a 24 hour period.

4. A system according to claim 1, wherein
said threshold value is derived from recorded displacement signal data of said tissue wall for said patient.

5. A system according to claim 1, wherein
said threshold value is derived from recorded displacement signal data of a tissue wall for a population of patients.

6. A system according to claim 5, wherein
said population of patients has similar demographic characteristics including at least two of, (a) age, (b) weight, (c) gender and (d) height, to those of said patient.

7. A system according to claim 1, wherein
said signal processor dynamically adjusts said threshold value in response to a determined sensitivity of arrhythmia detection.

8. A system according to claim 1, wherein
said signal processor determines said tissue wall displacement value at a predetermined point of a heart beat cycle in response to a synchronization signal.

9. A system according to claim 8, wherein
said signal indicating displacement of a tissue wall comprises a digitized electrical signal.

10. A system according to claim 1, wherein
said signal processor determines a displacement value in the displacement signal comprising a peak to peak displacement value.

11. A system according to claim 1, wherein
said signal processor calculates the displacement value by averaging a plurality of corresponding respective displacement values determined at substantially the same point in a heart cycle and over a plurality of heart cycles.

12. A system according to claim 1, wherein
said signal processor determines a displacement value in the displacement signal comprising at least one of, (a) a second highest peak to peak displacement value and (b) a third highest peak to peak displacement value indicating a tissue wall displacement occurring at a point within a heart cycle.

13. A system according to claim 1, including
a repository of predetermined mapping information, associating ranges of the displacement value or values derived from the displacement value, with corresponding medical conditions and
said comparator compares the displacement value or values derived from the displacement value, with said ranges to provide a comparison indicator identifying a medical condition and
said patient monitor generates an alert message identifying said medical condition.

14. A system according to claim 13, wherein
said predetermined mapping information associates ranges of the displacement value or values derived from the displacement value, with particular patient demographic characteristics and with corresponding medical conditions and said system uses patient demographic data including at least one of, age, weight, gender and height in comparing the displacement value or values derived from the displacement value with said ranges.

15. A system according to claim 1, wherein
said ultrasound device emits ultrasound wave signals within patient anatomy and acquires corresponding ultrasound echo signals at a sampling rate of 50-2000 Hz.

16. A system according to claim 1, wherein
said signal processor determines the displacement value in the displacement signal and derives at least one value from the displacement value, the at least one derived value including at least one of, (a) an averaged displacement value determined by averaging a plurality of corresponding respective displacement values determined at substantially the same point in heart cycle and over a plurality of heart cycles and (b) a standard deviation of the displacement value for a particular heart cycle.

17. A system according to claim 1, wherein
said signal processor derives at least one value from the displacement value including at least one of, $$\text{Amplitude change: } \Delta\% \ (A_i(t)) = \left| \frac{E_{A_i(t)} - E_{A_i(base)}}{E_{A_i(base)}} \right| \quad (a)$$

$$\text{Standard deviation change: } \Delta\% \ (\delta(t)) = \left| \frac{\delta_{A_i(t)} - \delta_{A_i(base)}}{\delta_{A_i(base)}} \right| \quad (b)$$

and $$\text{Wave variation: } \text{Var}(A_i(t)) = \left| \frac{E_{A_i(t)}}{\delta_{A_i(t)}} \right| \quad (c)$$

where, for each wave Ai, $E_{A_i}$ is an averaged amplitude, $\delta_i$ is a standard deviation for the wave and $A_i$ (base) is the waveform Ai in a preselected reference signal.

18. A system according to claim 1, wherein
said plurality of sensors are arranged substantially symmetrically within a catheter for emitting the ultrasound wave signals substantially perpendicular to a catheter longitudinal axis and acquiring the corresponding ultrasound echo signals to determine vessel wall dynamic movement over a heart cycle or respiratory cycle.

19. A system according to claim 1, wherein the plurality of sensors are configured to acquire the corresponding ultrasound echo signals covering 360 degrees of an internal circumference of a tissue wall of the vessel.

20. A system according to claim 1, wherein the signal processor is further configured to acquire the corresponding ultrasound echo signals on a plurality of channels from multiple vessel sites and de-convolute the acquired corresponding ultrasound echo signals to provide ultrasound waveform data of selected points of a vessel wall.

21. A system according to claim 20, wherein the signal processor is further configured to analyze the corresponding ultrasound echo signals in a time domain and a frequency domain for each of the plurality of channels.

* * * * *